United States Patent [19]

Vance et al.

[11] Patent Number: 5,939,541
[45] Date of Patent: Aug. 17, 1999

[54] METHOD FOR ENHANCING EXPRESSION OF A FOREIGN OR ENDOGENOUS GENE PRODUCT IN PLANTS

[75] Inventors: Vicki B. Vance; Gail J. Pruss, both of Columbia, S.C.; William O. Dawson, Winter Haven, Fla.; James Carrington, Pullman, Wash.; Laszlo Marton, Columbia, S.C.

[73] Assignee: University of South Carolina, Columbia, S.C.

[21] Appl. No.: 08/827,575

[22] Filed: Mar. 28, 1997

[51] Int. Cl.$^6$ .............................. C12N 15/40; C12N 5/04; C12N 15/82; A01H 5/00
[52] U.S. Cl. .................. 536/24.1; 435/320.1; 435/411; 435/468; 800/287; 800/288; 536/23.72
[58] Field of Search ................................. 536/24.1, 23.72; 435/320.1, 468, 411; 800/280, 287, 288

[56] References Cited

U.S. PATENT DOCUMENTS 4,855,237   8/1989   Morinaga et al. .
5,316,931   5/1994   Donson et al. .
5,589,367   12/1996  Donson et al. .

FOREIGN PATENT DOCUMENTS 9512669   5/1995   WIPO .
9704122   2/1997   WIPO .

OTHER PUBLICATIONS

Pugin et al. Molecular biology. 1994. vol. 28: 493–498.
Napoli et al. The Plant Cell. 1989. vol. 2: 278–289.
Pooggin et al. Molecular and General Genetics. 1992. vol. 234: 329–331.
Kumagai et al. Proc. Natl. Acad. Sci. 1993. vol. 90: 427–430.
Nicolaisen M. et al.: "The 5' Untranslated Region from Pea Seedborne Mosaic Potyvirus Rna as a Translational Enhancer in Pea and Tobacco Protoplasts", FEBS Letters, vol. 303, No. 2–3, 1992, pp. 169–172, XP002078747, Amsterdam NL.
Pruss G. et al: "Plant Viral Synergism: the Potyviral Genome Encodes a Broad–range Pathogenicity Enhancer That Trans-activated Replication of Heterologous Viruses" Plant Cell, vol. 9, No. 6, Jun. 1997, pp. 859–868, XP002078748 MD US.
Mazier M. et al: "Enhancement of Translational Activity Mediated by a Potyviral 5' Untranslated Sequence in Vivo but Not in Vitro" Comptes Rendus de l'Academie des Sciences. Serie III. Sciences de la Vie, vol. 317, No. 12—1994, pp. 1065–1072, XP002078749.
Timmer R.T. et al: "The 5' and 3' Untranslated Regions of Satellite Tobacco Necrosis Virus RNA Affect Translational Efficiency and Dependence on a 5' Cap Structure" Journal of Biological Chemistry, vol. 268, No. 13, May 5, 1993, pp. 9504–9510, XP002043707.
Turner R. and Foster G.: "The potential exploitation of plant viral translational enhancers in biotechnology for Increased Gene Expression" Molecular Biotechnology, vol. 3, 1995, pp. 225–236, XP002078750.
Takamatsu et al: "Production of Enkephalin in Tobacco Protoplasts Using Tobacco Mosaic Virus RNA Vector" FEBS Letters, vol. 269, pp. 73–76 (1990).
Hamamoto et al: "A New Tobacco Mosaic Virus Vector and Its Use for the Systemic Production of Angiotensin–I–Converting Inhibitor in Transgenic Tobacco and Tomato" Bio/Technology, vol. 11, pp. 930–932 (1993).
Kumagai et al: "Rapid, High–Level Expression of Biologically Active α–Trichosanthin in Transfected Plants by an RNA–Viral Vector" Proc. Natl. Acad. Sci. USA, vol. 90, pp. 427–430 (1993).
Dolia et al: "Tagging of Plant Potyvirus Replication and Movement by Insertion of β–Glucuronidase into the Viral Polyprotein" Proc. Natl. Acad. Sci., vol. 89, pp. 10208–10212 (1992).
Chapman et al: "Potato Virus X as a Vector for Gene Expression in Plants" The Plant Journal, vol. 2, pp. 549–557 (1992).
Vance et al: "5' Proximal Potyviral Sequences Mediate Potato Virus X/Potyviral Synergistic Diseases in Transgenic Tobacco" Virology, vol. 206, pp. 583–590 (1995).
Carrington, J.C. et al: "Expression of Potyviral Polyproteins in Transgenic Plants Reveals Three Proteolytic Activities Required for Complete Processing" EMBO J., vol. 9, pp. 1347–1353 (1990).
Chinnadurai: "Modulation of HIV–Enhancer Activity by Heterologous Agents: A Minireview" Gene, vol. 101, pp. 165–170 (1991).
Kim et al: "Essential Role of NF–kappa B in Transactivation of the Human Immunodeficiency Virus Long Terminal Repeat by Human Cytomegalovirus 1E1 Protein" J. Gen. Virol., vol. 77, pp. 83–91 (1996).
Baulcombe: "Mechanisms of Pathogen Derived Resistance to Viruses in Transgenic Plants" Plant Cell, vol. 8, pp. 1833–1844 (1996).

(List continued on next page.)

*Primary Examiner*—David T. Fox
*Assistant Examiner*—Ousama Zaghmout
*Attorney, Agent, or Firm*—Dority & Manning, P.A.

[57] ABSTRACT

The present invention provides a method for enhancing the expression of genes in plants by supplying a virally encoded booster sequence comprising the 5' proximal region of the potyvirus genome to the plant. The booster sequence enhances the expression of foreign genes or endogenous plant genes in plants by employing any known methodology of expressing introduced genes in plants. The booster sequence may be used to enhance expression of any gene, including foreign genes or endogenous plant genes, introduced by means of stable transformation into the genome of the plant or introduced by expression from a plant viral expression vector.

22 Claims, 6 Drawing Sheets

OTHER PUBLICATIONS

Lindbo et al: "Induction of a Highly Specific Antiviral State in Transgenic Plants: Implications for Regulation of Gene Expression and Virus Resistance" Plant Cell, vol. 5, pp. 1749–1759 (1993).

Mueller et al: "Homology–Dependent Resistance: Transgenic Virus Resistance in Plants Related to Homology Dependent Gene Silencing" Plant Cell, vol. 7, pp. 1001–1013 (1995).

Smith et al: "Transgenic Plant Virus Resistance Mediated by Untranslatable Sense RNAs: Expression, Regulation, and Fate of Nonessential RNAs" Plant Cell, vol. 6, pp. 1441–1453 (1994).

English et al: "Suppression of Virus Accumulation in Transgenic Plants Exhibiting Silencing of Nuclear Genes" Plant Cell, vol. 8, pp. 179–188 (1996).

Goodwin et al: "Genetic and Biochemical Dissection of Transgenic RNA–Mediated Virus Resistance" Plant Cell, vol. 8, pp. 95–105 (1996).

de Carvalho Niebel et al, "Post–Transcriptional Cosuppression of β–1, 3–Glucanase Genes Does Not Affect Accumulation of Transgene Nuclear RNA" Plant Cell, vol. 7, pp. 347–358 (1995).

Ingelbrecht et al: "Postranscriptional Silencing of Reporter Transgenes in Tobacco Correlates with DNA Methylation" Proc. Natl. Acad. Sci. USA, vol. 91, pp. 10502–10506 (1994).

Verchot et al: "The 35–kDa Protein from the N–Terminus of the Potyviral Polyprotein Functions as a Third Virus–Encoded Proteinase" Virology, vol. 185, pp. 527–535 (1991).

Verchot and Carrington: "Evidence that the Potyvirus P1 Proteinase Functions in Trans as an Accessory Factor for Genome Amplification" J. Virol, vol. 69, pp. 3668–3674 (1995).

Brantley and Hunt: "The N–Terminal Protein of the Polyprotein Encoded by the Potyvirus Tobacco Vein Mottling Virus is an RNA–Binding Protein" J. Gen. Virol., vol. 74, pp. 1157–1162 (1993).

Maia et al: "Potyviral HC–Pro: A Multifunctional Protein" J. Gen. Virol., vol. 77, pp. 1335–1341 (1996).

Sriskanda, V. S. et al: "An Eight Nucleotide Sequence in the Potato Virus X 3'–UTR is Required for Both Host Protein Binding and Viral Multiplication" J. Virol., vol. 70, pp. 5266–5271 (1996).

Kavanaugh et al: "Molecular Analysis of a Resistance Breaking Strain of Potato Virus X" Virology, vol. 189, pp. 609–617 (1992).

Donson et al: "Systemic Expression of a Bacterial Gene by a Tobacco Mosaic Virus–Based Vector" Proc. Natl. Acad. Sci. USA, vol. 88, pp. 7204–7208 (1991).

Sugiyama et al: "Systematic Production of Foreign Peptides on the Particle Surface of Tobacco Mosaic Virus" FEBS Letters, vol. 359, pp. 247–250 (1995).

Shi, X.M., et al: "Mutations in the Region Encoding the Central Domain of Helper Component–Proteinase (HC–Pro) Eliminate Potato Virus X/Potyviral Synergism" Virology, vol. 231, pp. 35–42 (1997).

Nobuhiko Takamatsu et al., "Production of enkephalin in tobacco protoplasts using tobacco mosaic virus RNA vector," Federation of European Biochemical Societies, 1990, vol. 269, No. 1, 73–76.

J. Donson et al., "Systemic expression of a bacterial gene by a tobacco mosaic virus–based vector," Proc. Natl. Acad. Sci. USA, Aug. 1991, vol. 88, pp. 7204–7208.

Valerian V. Dolja et al., "Tagging of plant potyvirus replication and movement by insertion of β–glucuronidase into the viral polyprotein," Proc. Natl. Acad. Sci. USA, Nov. 1992, vol. 89, pp. 10208–10212.

Sean Chapman et al., "Potato virus X as a vector for gene expression in plants," The Plant Journal, 1992, 2(4), pp. 549–557.

M.H. Kumagai et al., "Rapid, high–level expression of biologically active α–trichosanthin in transfected plants by an RNA viral vector," Proc. Natl. Acad. Sci. USA, Jan. 1993, vol. 90, pp. 427–430.

Hiroshi Hamamoto et al., "A New Tobacco Mosaic Virus Vector and its Use for the Systemic Production of Antiotensin–I–Converting Enzyme Inhibitor in Transgenic Tobacco and Tomato," Bio/Technology, Aug. 1993, vol. 11, pp. 930–932.

Yoshinori Sugiyama et al., "Systemic production of foreign peptides on the particle surface of tobacco mosaic virus," Federation of European Biochemical Societies 359, 1995, pp. 247–250.

Vicki Bowman Vance et al., "5' Proximal Potyviral Sequences Mediate Potato Virus X/Potyviral Synergistic Disease in Transgenic Tobacco," Virology 206, 1995, pp. 583–590.

David C. Baulcombe et al., "Jellyfish green fluorescent protein as a reporter for virus infections," The Plant Journal 7(6), 1995, pp. 1045–1053.

Robert W. M. Sablowski et al., "Expression of a flower–specific Myb protein in leaf cells using a viral vector causes ectopic activation of a target promoter," Proc. Natl. Acad. Sci. USA, Jul. 1995, vol. 92, pp. 6901–6905.

Caius M. T. Rommens et al., "Use of a Gene Expression System Based on Potato Virus X to Rapidly Identify and Characterize a Tomato Pto Homolog That Controls Fenthion Sensitivity," The Plant Cell, Mar. 1995, vol. 7, pp. 249–257.

Thomas H. Turpen et al., "Malaria Epitopes Expressed on the Surface of Recombinant Tobacco Mosaic Virus," Bio/Technology, Jan. 1995, vol. 13, pp. 53–57.

Steven J. Casper et al., "Expression of the green fluorescent protein–encoding gene from a tobacco mosaic virus–based vector," Gene 173, 1996, pp. 69–73.

Vicki Bowman Vance, "Replication of Potato Virus X RNA is Altered in Coinfections with Potato Virus Y," Virology 182, 1991, pp. 486–494.

FIGURES 1(A), (B), (C), (D)

| TRANSGENE MUTANT | AA LOCATION | SYNERGISM |
|---|---|---|
| B | 157 (P-1) | + |
| C | 188 (P-1) | + |
| E | 247 (P-1) | + |
| I | 366 (HC-Pro) | + |
| K | 426 (HC-Pro) | - |
| L | 456 (HC-Pro) | - |

A
PVX-5'TEV
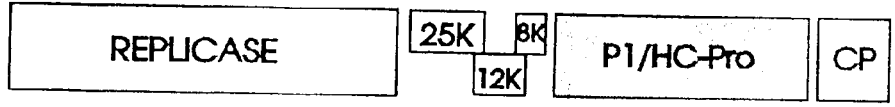
PVX-HC
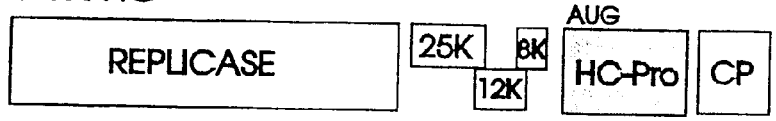
PVX-noHC
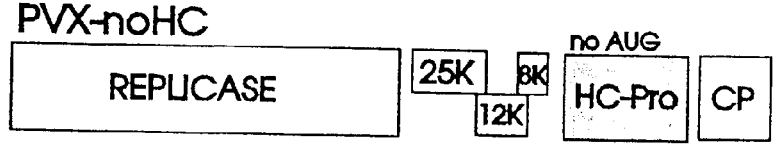
B 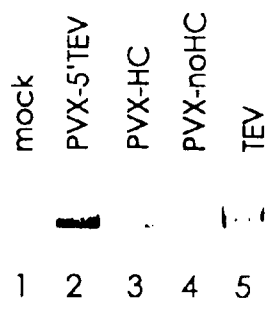
C 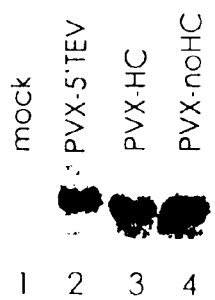
FIGURES 3(A), (B), (C)

|            | (−) RNA   | (+) RNA   |
|------------|-----------|-----------|
| PVX-5'TEV  |           |           |
| PVX-HC     |           |           |
| PVX-noHC   |           |           |
|            | 1  2  3   | 1  2  3   |

FIGURE 4

METHOD FOR ENHANCING EXPRESSION OF A FOREIGN OR ENDOGENOUS GENE PRODUCT IN PLANTS

FIELD OF THE INVENTION

The present invention is directed to the field of producing gene products from plants. Specifically, the invention relates to methods of enhancing the expression of either foreign or endogenous genes introduced into plants.

BACKGROUND OF THE INVENTION

For purposes of this specification, the term "gene" or "genes" is used to mean nucleic acid sequences (including both RNA or DNA) that encode genetic information for the synthesis of a whole RNA, a whole protein, or any portion of such whole RNA or whole protein. Genes that are not part of a particular plant's genome are referred to as "foreign genes" and genes that are a part of a particular plant's genome are referred to as "endogenous genes". The term "gene products" refers to RNAs or proteins that are encoded by the gene. "Foreign gene products" are RNA or proteins encoded by foreign genes and "endogenous gene products" are RNA or proteins encoded by endogenous genes.

It has been known for some time that plants may be used to express foreign gene products, or to overexpress endogenous gene products, via introduction of the foreign or endogenous gene into a plant through the use of various biotechnological methods. In one biotechnological approach, the gene encoding the gene product of interest is introduced into the plant genome under control of a promoter sequence that is functional in the plant, resulting in the transcription of the gene to produce messenger RNA, followed by various RNA processing events, exit of the RNA from the nucleus and translation of the messenger RNA to produce the encoded protein. This approach has been exploited by agricultural and industrial interests to provide a ready and relatively inexpensive source of a variety of beneficial gene products.

In some cases the gene products serve their function in the plant from which they are expressed. A natural insecticide that confers resistance to insects in commercially available transgenic crop plants is one such example. In other cases, the gene product of interest may be extracted from the plant and serves its function elsewhere. For example, potentially valuable proteins, such as antibodies, may be expressed in plants. Such production methods are seen as a marked improvement over the use of animal tissue for such production.

Several years after the first series of publications detailing methods to introduce foreign genes or additional copies of endogenous genes into plants, an unexplained phenomenon was reported. Plants containing an additional copy of an endogenous plant gene not only failed to display the hoped for enhancement in the accumulation of the gene product, but also repressed expression of the endogenous gene, effectively eliminating the expression of the endogenous gene product. This phenomenon was referred to as "cosuppression" since expression of both the endogenous gene and the introduced transgene were suppressed. The incidence of cosuppression in transformed plants containing extra copies of an endogenous gene is high. Up to 90% of independently transformed petunia plants containing an introduced chalcone synthase gene show some variegation in petal color, which is indicative of cosuppression of this gene. It has been postulated that this same type of gene expression suppression may occur whenever a particular messenger RNA sequence is expressed at high levels. This may explain the generally low levels of expression of introduced genes in plants.

Whatever the explanation, the inactivation of gene expression by cosuppression is a problem in cases where high levels of expression of an introduced gene or over expression of an endogenous gene is desirable. Thus, the use of transgenic plants to express introduced genes has been limited due to this general constraint on high level gene expression in the plant cells.

Another approach to expressing foreign or endogenous gene products in plants is the use of plant viruses as vectors to express foreign genes in an appropriate host plant. One example of a viral vector for expressing a foreign gene is described in U.S. Pat. Nos. 5,316,931 and 5,589,367, both naming Donson et al. as inventors. Both of these patents are incorporated in their entireties herein by reference. These patents provide recombinant plant viral nucleic acids and recombinant viruses that are stable for maintenance and transcription or expression of non-native (foreign) nucleic acid sequences and which are capable of systemically transcribing or expressing the foreign sequences in the host plant.

Others have also attempted to use various viral-based vectors to express genes that are not native to the virus. For example, Takamatsu et al. described the use of tobacco mosaic virus ("TMV") as a vector to express enkephalin in "Production of Enkephalin in Tobacco Protoplasts Using Tobacco Mosaic Virus RNA Vector," 269 FEBS Lett., 73–76 (1990). In 1993, Hamamoto et al. described the production of an angiotensin-I-converting enzyme inhibitor peptide from a TMV RNA vector in "A New Tobacco Mosaic Virus Vector and Its Use for the Systemic Production of Angiotensin-I-Converting Inhibitor in Transgenic Tobacco and Tomato," 11 Bio/Technology, 930–932 (1993). Kumagai, et al. disclosed using a tobamovirus as a viral vector to produce an HIV-inhibitor, α-Trichosanthin in "Rapid, High-Level Expression of Biologically Active α-Trichosanthin in Transfected Plants by an RNA-Viral Vector," 90 Proc. Natl. Acad. Sci. USA, 427–430 (1993).

Other examples of using viral vectors to express foreign gene products by various methods are known to those of skill in the art. Generally, suitable plant viral vectors for expressing foreign genes should be self-replicating, capable of systemic infection in a host, and stable. In addition, they should be capable of containing the nucleic acid sequences that are foreign to the native virus forming the vector.

Although using plant viruses to express foreign gene products generally allows expression of the products at a higher level than that obtained from genes introduced stably in the plant genome, current methods of expressing genes from viral vectors suffer from several practical limitations. The virus is often debilitated when a foreign gene is cloned into it. When a foreign gene sequence (one not native to the virus vector) is introduced into a virus, the virus is weakened and the weakened virus does not produce its gene products as readily. In addition to debilitation of viral gene expression, the virus is unable to replicate and move as efficiently through the host plant as can wild-type parental viruses. Furthermore, viruses carrying foreign genes tend to be unstable and often delete the inserted genes as the viruses replicate. These tendencies are discussed in Dolia, et al., "Tagging of Plant Potyvirus Replication and Movement by Insertion of β-Glucuronidase into the Viral Polyprotein," 89 Proc. Natl. Acad. Sci. USA, 10208–10212 (1992) and Chapman et al., "Potato Virus X as a Vector for Gene Expression in Plants, 2 The Plant Journal, 549–557 (1992).

It has also been known for some time that in plants infected with more than one virus at the same time, the two co-infecting viruses may interact synergistically to cause a more severe disease in the plant than does either virus alone. In many cases it has been shown that the increase in severity of host symptoms correlates with an increase in the accumulation of one virus of the synergistic pair. For example, it is known that a synergistic disease is caused by the interaction of potato virus X ("PVX") and potato virus Y ("PVY"). PVX in such synergistically-diseased plants accumulates to a higher level than in singly infected plants and eventually causes the first systemically infected leaves of the doubly infected plant to die. The infection by either PVX or PVY alone in the same plant has little or no effect at all.

These synergistic effects have also been demonstrated as a result of PVX interaction with at least three other members of the potyvirus group of plant viruses,-tobacco vein mottling virus ("TVMV"), tobacco etch virus ("TEV"), and pepper mottle virus ("PepMoV"). Such PVX/potyvirus mixed infections of a tobacco host plant result in a dramatic increase in accumulation of PVX particles (up to ten-fold), with no corresponding increase or decrease in accumulation of the potyvirus particles. These PVX/potyviral mixed infections also result in a dramatic increase in disease symptoms in the doubly infected plant.

The initial step in the present discovery of the viral booster sequence was the finding that the PVX/potyviral synergistic disease syndrome, characterized by increases in symptom severity and in accumulation of the PVX pathogen, does not require infection with both viruses. This was reported by Vance, et al. in "5' Proximal Potyviral Sequences Mediate Potato Virus X/Potyviral Synergistic Disease in Transgenic Tobacco," 206 *Virology*, 583–590 (1995). The synergistic disease is mimicked in plants expressing only a subset of the potyviral genomic RNA and infected singly with PVX. The potyviral region shown to mediate the synergistic disease comprises the 5'-proximal 2780 nucleotides of the genomic RNA, including the 5'-untranslated region (5'-UTR) and the region encoding the potyviral gene products P1, helper component-proteinase (HC-Pro) and a portion of P3. This described potyviral region is referred to herein as the "P1/HC-Pro sequence".

Thus, Vance, et al. (1995), identified a disease determinant carried by the potyvirus genome (the P1/HC-Pro sequence), and this disease determinant was shown to mediate the well-known PVX/potyviral synergistic disease. Although the mechanism by which this potyviral sequence mediated the PVX/potyviral synergistic disease was unknown, it was postulated to involve a specific, direct interaction of the potyviral P1/HC-Pro RNA sequence or the encoded potyviral gene products with the genomic RNA or replication proteins of the interacting PVX pathogen. Although the potyviral P1/HC-Pro sequence was found to boost accumulation of the PVX viral structural gene (coat protein) and the accumulation of the PVX viral particle, this enhanced accumulation was thought to be specific for the native PVX genes expressed from the native PVX genome. Furthermore, the enhanced accumulation of PVX coat protein and PVX virus particles was tightly correlated with the perceived detrimental and undesirable increase in disease symptoms.

Although PVX and other viruses, such as cauliflower mosaic virus, the geminiviruses, and TMV, have been used as viral vectors for expressing foreign gene products, such vectors have not been completely successful as mentioned above. Although gene products have been produced via expression from viral vectors, the usefulness of such vectors is limited by instability of inserted sequences and the failure of the viral vector to replicate efficiently. Expression of gene products from genes introduced stably into the plant genome also suffers from limitations as mentioned above.

Accordingly, it would be beneficial if methods of producing gene products from plants could be developed to allow enhanced expression of the introduced gene from stably transformed plants and enhanced expression of genes introduced into a plant via a plant viral vector, while retaining stability of the introduced sequence to ensure accumulation of the gene product. The present invention overcomes some of the deficiencies of prior gene product expression methods by using a particular boosting sequence obtained from a potyvirus.

SUMMARY OF THE INVENTION

It is an object of the present invention to provide methods for enhancing the expression of gene products in plants.

Another object of the present invention is to provide methods of enhancing the expression of introduced foreign and endogenous gene products in plants.

A further object of the present invention is to provide processes using a particular booster sequence to enhance the expression of an introduced gene product in a plant.

These and other objects are achieved by providing a method for enhancing the expression of genes in plants by supplying a virally encoded booster sequence comprising the 5' proximal region of the potyvirus genome, which may include the coding region for P1, helper component-proteinase (HC-Pro), and a small portion of P3. Some portion of the booster sequence may be expressed either individually or fused to other sequences, a modified version of the booster sequence, a related sequence from another virus or any portion or modified version of that related sequence expressed either individually or fused to another sequence. The booster sequence enhances the expression of foreign genes or endogenous plant genes that are introduced to the plant by employing any known methodology. One example of such known methods include the expression of introduced genes from one or more copies of a gene stably incorporated into the plant genome. Another example of such known methods is the expression of genes introduced via plant viral expression vectors.

The process of enhancing gene expression may be carried out in various forms. For example, the booster sequence may be provided to the plant in a variety of ways. It may be provided by infection with a virus that expresses the booster sequence as a native viral gene product during its natural life cycle. Alternatively, the booster sequence may be introduced through use of a transgenic host plant expressing the booster sequence as an introduced gene. The booster sequence may also be introduced using the same viral expression vector utilized to express the introduced foreign or endogenous gene of interest. A transient expression system may be employed to temporarily express the booster sequence or a two-component co-infection system may be used wherein two viruses are required for successful boosting of gene expression. In the two-component co-infection system, one virus expresses the booster sequence while the other virus expresses the introduced gene of interest.

In addition, the booster sequence may be used to enhance expression of any introduced gene, including foreign genes or endogenous plant genes. The genes to be boosted may be introduced to the plant in a variety of ways. Foreign or endogenous genes may be introduced by means of stable transformation into the genome of the plant employing any of the known technologies used for this process. Alternatively the foreign or endogenous gene may be introduced using any plant viral expression vector.

More specifically, the present invention involves a method of expressing a foreign gene or an endogenous plant gene that has been introduced into plant material, which includes plant cells, plant protoplasts, or whole plants, wherein the improvement comprises the supplying of a booster sequence comprising a portion of the 5' proximal region of the genome of a potyvirus to the plant material so that expression of said foreign gene or endogenous plant gene is enhanced. The plant gene may be a foreign gene not naturally occurring in the plant material prior to being introduced therein, or an endogenous plant gene that was naturally occurring in the plant material prior to being introduced as an additional copy or additional copies of the endogenous gene. The 5' proximal region supplied may comprise the coding region for P1, helper component-proteinase (HC-Pro) and a small portion of P3 and the portion of the 5' proximal region may be expressed independently or fused to other sequences.

The foreign or endogenous gene may be introduced to the plant via a viral expression vector with the booster sequence being supplied by expression from the same viral vector; introduced via a viral expression vector with the booster sequence being supplied by expression of one or more DNA copies of the booster sequence stably incorporated into the plant's genome; or introduced via a viral expression vector with the booster sequence being expressed from a transient expression system containing one or more DNA copies of said booster sequence. A two-component viral vector system may be utilized with one viral component expressing the booster sequence and the other viral component expressing the introduced gene. The introduced gene may be a foreign gene or endogenous plant gene introduced via a viral expression vector with the booster sequence being supplied by co-infection with a potyvirus that expresses the native booster sequence encoded by that potyvirus; introduced via a viral expression vector with the booster sequence being supplied by co-infection with a potyvirus that expresses a nonnative version of said booster sequence; or introduced via a viral expression vector having the gene fused to the structural gene of said viral expression vector.

In addition the foreign gene or endogenous plant gene may be introduced to a plant genome via any mode of stable transformation of one or more DNA copies of the introduced gene, with the booster sequence being supplied prior to, during, or after introduction of the foreign gene or endogenous plant gene via stable transformation procedures so that it enhances either the expression of the introduced gene product or the number or proportion of transformant plants that express the introduced gene product. In this aspect, the booster sequence may be supplied via expression from one or more DNA copies of the booster sequence stably incorporated into the plant genome prior to, during, or after transformation of the plant material with said introduced gene product.

BRIEF DESCRIPTION OF THE FIGURES

The file of this patent contains at least one drawing executed in color. Copies of this patent with color drawings will be provided by the Patent and Trademark Office upon request and payment of the necessary fee.

A full and enabling disclosure of the present invention, including the best mode thereof, to one of ordinary skill in the art, is set forth more particularly in the remainder of the specification, including reference to the accompanying figures, in which:

FIGS. 1(A) and 1(C) show control tobacco plants which do not express the booster sequence and are infected, either CMV(1(A)) or TMV (1(C)).

FIGS. 1(B) and 1(D) show TEV-transformed line U-6B plants expressing the 5' proximal region of the TEV genome and infected with either CMV (1(B)) or TMV (1(D)).

FIGS. 3A–3C are a diagram of PVX vectors used to express TEV sequences.

FIG. 3(A) is a diagram of PVX viral genomic RNAs carrying TEV 5' proximal sequences, with PVX-5'TEV having nucleotides 146 to 2674 of TEV encoding P1, HC-Pro, and part of P3, PVX-HC carrying the region encoding HC-Pro plus appropriate translation start and stop codons, and PVX-noHC being the same as PVX-HC except that the initial AUG has been changed to ACG.

FIG. 3(B) shows a protein gel blot showing the level of HC-Pro in mock infected *N. benthamiana* leaves (lane 1) or in leaves systemically infected with either PVX-5'TEV (lane 2), PVX-HC (lane 3), PVX-noHC (lane 4), or TEV (lane 5).

FIG. 3(C) shows a Northern blot of RNA isolated from leaves as given for the protein gel blot of FIG. 3(B) and hybridized with a radioactive probe specific for the TEV HC-Pro sequence.

FIG. 4 shows the kinetics of accumulation of PVX (−) strand RNA altered by expression of the TEV P1/HC-Pro sequence, so that the level of RNA accumulation is boosted and further showing RNA gel blot analysis of (+) and (−) strand viral RNAs from tobacco protoplasts infected with PVX-5'TEV (top row), PVX-HC (middle row) or PVX-noHC (bottom row) at 24 (lane 1), 48 (lane 2), or 72 (lane 3) hrs after inoculation, wherein the left panel is (−) strand viral RNA and the right panel is (+) strand viral RNA. In this Figure, total RNA had been isolated from protoplasts, fractionated by denaturing agarose gel electrophoresis, transferred to nylon membrane, and hybridized with radioactive probes specific to either the PVX (+) strand RNA (right panel) or (−) strand RNA (left panel) and the regions of the blots containing genomic-length RNAs are shown.

FIG. 5 shows the relative levels of PVX (−) strand RNA at various times after infection of protoplasts with PVX-5'TEV, PVX-HC, or PVX-noHC, with the 48 and 72 hour values being normalized to the 24-hr time point and each time point being the average of two independent experiments.

FIG. 6 shows the timecourse of luciferase activity in protoplasts infected with PVX reporter viruses, with the PVX reporter viruses expressing the TEV P1/HC-Pro sequence (5'TEV) or a mutant version of that sequence [5'TEV(K)] that encodes an altered HC-Pro that fails to support synergism.

DETAILED DESCRIPTION OF PREFERRED EMBODIMENT

Other objects, features and aspects of the present invention are discussed in greater detail below. It is to be understood by one of ordinary skill in the art that the present discussion is a description of exemplary embodiments only and is not intended as limiting the broader aspects of the present invention, which broader aspects are embodied in the exemplary construction.

The present invention employs a virally encoded booster sequence comprising the 5' proximal region of the potyvirus genome, or some portion of or modified form thereof, supplied to a method for expressing a gene product in a plant. The booster sequence enhances the expression of the gene product and allows the product to accumulate within the plant.

Contrary to previous beliefs, the present invention has revealed that the potyviral P1/HC-Pro sequence is not merely the specific disease determinant for PVX/potyviral synergism. Instead, the potyviral P1/HC-Pro sequence functions in a general fashion, enhancing the accumulation and pathogenicity of a broad range of plant viruses.

The present invention has revealed that the P1/HC-Pro sequence not only enhances the expression of a native viral gene from its native viral genome, as shown by Vance, et al., (1995), for the expression of PVX coat protein, but also enhances the expression of foreign genes contained in a plant viral expression vector.

The present invention has also revealed that the boosting action of the P1/HC-Pro sequence may be separated from its detrimental effects on the plant. Experiments using genetically modified or fused versions of the potyviral P1/HC-Pro sequence have identified regions that are required for the desirable boosting activity of the sequence and regions that are required for the detrimental disease promoting action of the sequence. Although the two identified regions overlap, it is possible to modify the sequence such that the boosting action occurs without causing detrimental disease symptoms. Thus, the invention provides a method to enhance expression of any foreign or endogenous gene from a viral expression vector, using the boosting action of the sequence in the absence of detrimental effects on the host plant when such disease symptoms are deemed undesirable for the intended purpose.

The present invention has further revealed that the potyviral P1/HC-Pro sequence affects the expression of genes that have been introduced to the plant via stable incorporation into the plant genome. Thus, the booster sequence can reverse or inhibit the effects of the natural plant cosuppression system and enhance the expression of foreign or endogenous plant genes introduced by stable incorporation into the plant genome.

EXAMPLES 1–4

To determine whether the P1/HC-Pro sequence is involved in synergistic diseases other than the PVX/potyviral synergism, two other plant viruses, tobacco mosaic virus ("TMV") and cucumber mosaic virus ("CMV"), were employed. Both TMV and CMV have the ability to infect tobacco and are known to interact synergistically with a potyvirus.

Figure 1:
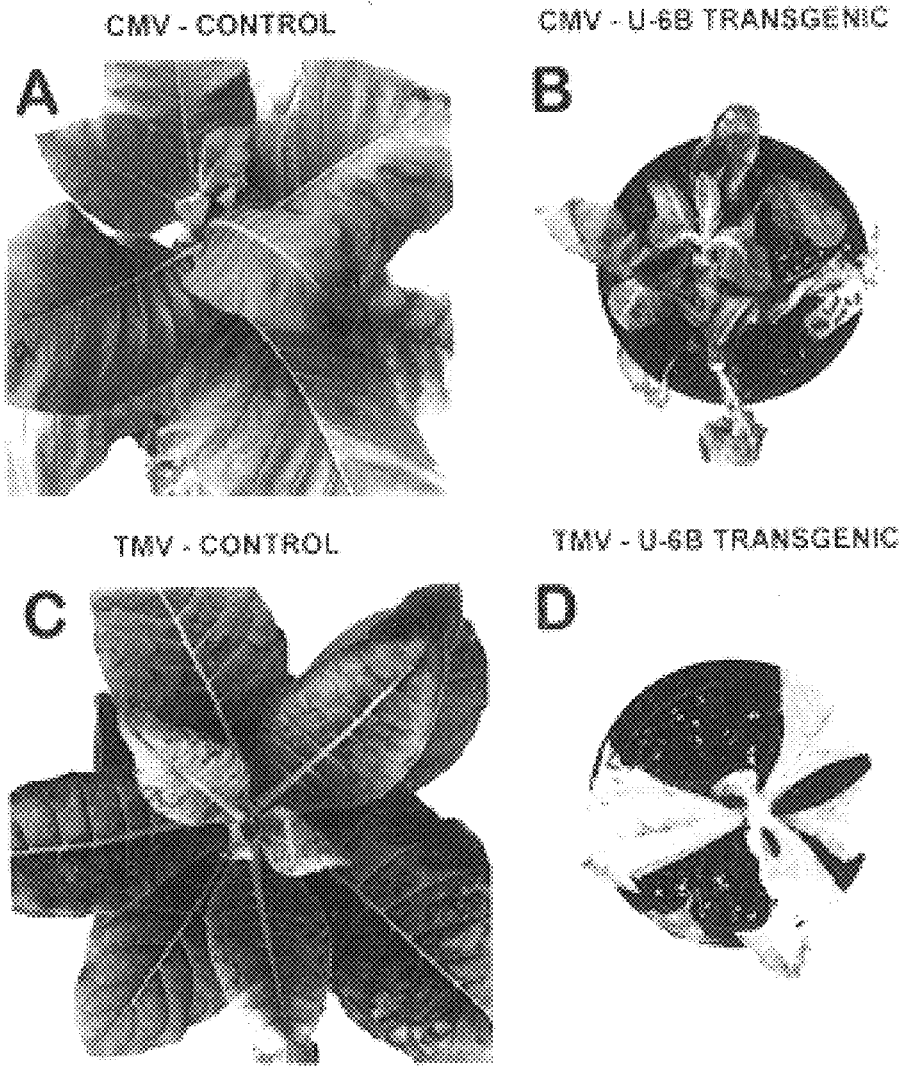
FIG. 1 shows the enhanced pathogenicity of CMV and TMV in transgenic tobacco expressing the potyviral P1/HC-Pro sequence.

Transgenic tobacco plants expressing the P1/HC-Pro sequence [transgenic line U-6B; described by Carrington, J. C., Freed, D. D. and Oh, C-S, "Expression of Potyviral Polyproteins in Transgenic Plants Reveals Three Proteolytic Activities Required for Complete Processing," 9 *EMBO J.*, 1347–1353 (1990) and Vance, V. B., Berger, P. H., Carrington, J. C., Hunt, A. G. and Shi, X. M, "5' Proximal Potyviral Sequences Mediate Potato Virus X/Potyviral Synergistic Disease in Transgenic Tobacco," 206 *Virology,* 583–590 (1995)] and control tobacco plants of the same line that did not express this sequence were inoculated with TMV and with CMV. Symptom development was monitored. After infection with either TMV or CMV, transgenic line U-6B developed symptoms which were dramatically different from and much more severe than those in the control plants as shown in FIG. 1. While both TMV and CMV induced relatively mild symptoms in the control tobacco plants (FIG. 1A and 1C, respectively), both viruses were lethal in the U-6B transgenic line, resulting in death of the plant after several weeks (FIG. 1B and 1D, respectively).

As in the previously known PVX/potyviral interaction, the level of accumulation of both the TMV and the CMV pathogens was enhanced by the presence of the potyviral P1/HC-Pro sequence. This result supports the conclusion that the potyviral P1/HC-Pro sequence acts in a general manner, enhancing the pathogenicity and accumulation of a broad range of viruses.

The P1/HC-Pro sequence alters host response to heterologous plant viruses from at least three different groups (PVX, potexvirus; TMV, tobamovirus and CMV, cucumovirus). The fact that expression of this potyviral sequence alters the disease process for each of these unrelated heterologous viruses indicates that the sequence affects a step in the infection process that is common to all these viruses. Each of these viruses is capable of interacting in a mixed infection with a member of the potyvirus group of plant viruses to induce synergistic diseases which occur in an evolutionary diverse range of host plants and involve interactions with a large number of plant viral groups. The potyviral P1/HC-Pro sequence mediates the enhanced pathogenicity and accumulation of virus in each of these synergies. Thus, the use of the presently described booster sequence (which is described herein and comprises the potyviral P1/HC-Pro sequence or any portion or modified version of that sequence) is applicable to a wide range of plant viral groups and host plants.

Because expression of the P1/HC-Pro sequence affects a broad range of heterologous viruses, it was deduced that the mechanism for these effects may involve an indirect interaction via a host factor common to all these tobacco infections, rather than a direct interaction with three different viral RNAs or gene products. Two different indirect mechanisms could explain transactivation of viral replication by P1/HC-Pro. The TEV sequence might increase the activity or availability of a positive regulator of viral replication that affects both TEV and heterologous viruses. The stimulation of one virus by a host factor induced by another virus has been shown in mixed infections with human cytomegalovirus (HCMV) and human immunodeficiency virus-1 (HIV-1), where HCMV can induce expression of host transcription factor NF-kappa B, which then activates HIV-1 replication (Chinnadurai, "A Modulation of HIV-Enhancer Activity by Heterologous Agents: A Minireview," 101 *Gene, 165–170* (1991); Kim et al., "Essential Role of NF-kappa B in Transactivation of the Human Immunodefiency Virus Long Terminal Repeat by Human Cytomegalovirus 1E1 Protein," 77 *J. Gen. Virol.,* 83–91 (1996). Alternatively, the P1/HC-Pro sequence might interfere with the activity or availability of a negative regulator of viral replication, perhaps part of a host defense system that normally limits viral accumulation. Because HC-Pro enhances the accumulation of a broad range of viruses and acts at the level of viral replication, the putative host defense system would necessarily be general in nature and act at the single cell level. A host system consistent with these requirements has been proposed as the underlying mode of action in sense RNA-mediated virus resistance in transgenic plants (Baulcombe, "Mechanisms of Pathogen Derived Resistance to Viruses in Transgenic Plants," 8 *Plant Cell,* 1833–1844 (1996); Lindbo et al., "Induction of a Highly Specific Antiviral State in Transgenic Plants: Implications for Regulation of Gene Expression and Virus Resistance," 5 *Plant Cell,* 1749–1759 (1993); Mueller et al., "Homology-Dependent Resistance: Transgenic Virus Resistance in Plants Related to Homology Dependent Gene Silencing," 7 *Plant Cell,* 1001–1013 (1995); Smith et al., "Transgenic Plant Virus Resistance Mediated by Nontranslatable Sense RNAs: Expression, Regulation, and Fate of Nonessential RNAs," 6 *Plant Cell,* 5266–5271 (1994). In this model, an RNA targeting system is activated by high level expression of a transgene that contains viral sequences. Once activated, the system rapidly destroys the specific viral RNA target, whether the RNA is expressed from the transgene or from a viral RNA template during viral replication (English et al.,"Suppression of Virus Accumulation in Transgenic Plants Exhibiting Silencing of Nuclear Genes," 8 *Plant Cell,* 179–188 (1996); Goodwin et al., "Genetic and Biochemical Dissection of Transgenic RNA-Mediated Virus Resistance," 8 *Plant Cell,* 95–105 (1996); Mueller et al. (1995). The same cellular system is also thought to be involved in post-transcriptional gene silencing (cosuppression) of nonviral transgenes in plants (Baulcombe (1996); de Carvalho Niebel et al., "Post-Transcriptional Cosuppression of β-1,3-Glucanase Genes Does Not Affect Accumulation of Transgene Nuclear RNA," 7 *Plant Cell,* 347–358 (1995); Ingelbrecht et al.,"Postranscriptional Silencing of Reporter Transgenes in Tobacco Correlates with DNA Methylation," 91 *Proc. Natl. Acad. Sci. USA,* 10502–10506 (1994). The experimental data below indicates that P1/HC-Pro boosts the expression of introduced genes in plants by interfering with the induction of this cosuppression pathway and thus allowing the messenger RNA of introduced genes to accumulate to high levels, resulting in the enhanced accumulation of the encoded gene product.

As discussed above, the potyviral booster sequence has been identified as the P1/HC-Pro sequence. This region is expressed initially as a polyprotein and subsequently processed by the proteolytic activities of both P1 and HC-Pro to produce the mature viral proteins. Both HC-Pro and P1 are multifunctional proteins. P1 has proteinase activity that cleaves the potyviral polyprotein, creating the carboxy-terminus of P1 and the amino-terminus of HC-Pro [Verchot et al., "The 35-kDa Protein from the N-Terminus of the Potyviral Polyprotein Functions as a Third Virus-Encoded Proteinase," 185 *Virology,* 527–535 (1991)]. P1 also functions in trans as an accessory factor for genome replication (Verchot and Carrington, "Evidence that the Potyvirus P1 Proteinase Functions as an Accessory Factor for Genome Amplification," 69 *J. Virol.,* 3668–3674 (1995) and has RNA binding activity (Brantley and Hunt, "The N-Terminal Protein of the Polyprotein Encoded by the Potyvirus Tobacco Vein Mottling Virus is an RNA-Binding Protein," 74 *J. Gen. Virol.,* 1157–1162 (1993)).

HC-Pro has at least three functional domains: an amino-terminal domain required for aphid transmission, a central domain involved in pathogenicity, RNA replication and leaf to leaf movement of the virus through the phloem, and a carboxy-terminal domain required for autoproteolytic processing of the HC-Pro carboxy-terminus (Maia et al., "Potyviral HC-Pro: A Multifunctional Protein," 77 *J. Gen. Virol.,* 1335–1341 (1996)). The central domain of HC-Pro is of particular interest because it is involved in the regulation of both pathogenicity and RNA replication of potyviruses and these are the characteristics that are altered in the heterologous virus during synergism.

EXAMPLES 5–7

Figure 2:
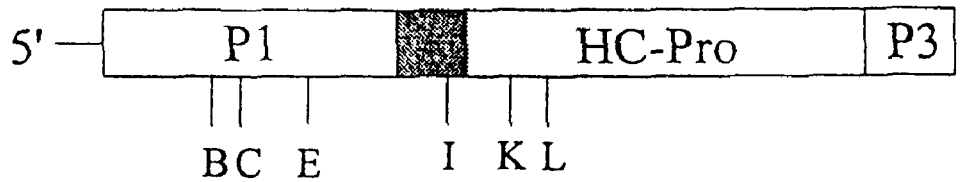
FIG. 2 is a diagram of the P1/HC-Pro region of the TEV genome showing the location of insertion mutations within the P1 and HC-Pro coding regions, with the locations of the resulting three amino acid insertions within the mutant polyprotein and the abilities of the mutant transgenes to induce synergistic disease being indicated below the diagram and the HC-Pro coding sequence deleted from TEV-2del being indicated by stippling.

In this Example, the effect of mutations in this potyviral sequence on the induction of synergistic disease was examined. Three transgenic tobacco lines expressing the TEV P1/HC-Pro sequence with mutations within the P1 coding region were not impaired in their ability to mediate synergism when infected with PVX. In contrast, two out of three transgenic lines with mutations in the HC-Pro coding region were unable to induce the synergistic increases in either symptom severity or PVX accumulation. Loss of boosting function was associated with mutations within the region encoding the central domain of HC-Pro, while the ability to induce synergism was retained in a transgenic line expressing HC-Pro with an alteration in the amino-terminal "zinc-finger domain". The location of the various mutations and their effect on synergism are shown in FIG. 2. In addition, sixteen out of twenty-five alanine scanning mutations affecting clusters of charged residues within the TEV HC-Pro coding sequence retained the ability to induce synergism. Furthermore, in co-inoculation experiments, a TEV mutant (TEV-del2) lacking the sequence encoding the zinc-finger domain of HC-Pro (FIG. 2) induced a typical synergistic response in interaction with PVX. The deleted version of the HC-Pro sequence carried by TEV-del2 is also fused with a partial sequence from the GUS gene.

These results indicate that the TEV P1/HC-Pro sequence encoding the central domain of HC-Pro is required for both the boosting capacity of the sequence and the enhanced pathogenicity conferred by the sequence. These results also indicate that the zinc-finger domain comprising the first 66 amino acid residues of HC-Pro is dispensable for both the boosting function and the detrimental increase in disease symptoms. Furthermore, the results indicate that many regions of the P1/HC-Pro sequence can be modified without affecting either boosting capacity or pathogenicity. The booster sequence may be completely functional as a fusion with another sequence (such as the GUS sequence as in the TEV-del2 mutant).

Finally, the results of this Example show that the booster sequence is active for boosting gene expression in a variety of modified forms or as a fusion protein with other proteins.

The present invention further involves enhancing the expression of a gene product in a plant through the use of the claimed booster sequence. Since it has been shown that the booster sequence containing various mutations and/or deletions or fused to another sequence is still functional for this purpose, the claimed booster sequence includes the P1/HC-Pro sequence from any potyvirus or closely related group of viruses, including the non-aphid borne potyviruslike viruses, or any modified form of this sequence including forms that have been mutated, deleted or fused to other sequences.

The following Examples describe an exemplary case where the domains of the P1/HC-Pro sequence required for pathogenicity and boosting capacity were identified using deletions of the region.

EXAMPLES 8–10

The P1/HC-Pro region of the TEV genome expressed in U-6B transgenic plants consists of 2670 nucleotides that include the 5'-UTR and the coding region for mature viral proteins P1 and HC-Pro, as well as a portion of P3. The proteins are expressed initially as a polyprotein and then processed by both P1 and HC-Pro autoproteolytic activities.

To determine if all or only part of this sequence is required for synergism, the ability of PVX to be used as a vector to express foreign genes was utilized to create PVX/TEV synergism in a system in which PVX itself expresses the P1/HC-Pro sequence. This system was then used to determine the minimum TEV sequence required for induction of synergism.

Three different PVX vectors were constructed by cloning various TEV sequences into a modified version (Sriskanda, V. S., Pruss, G., Ge, X., and Vance, V. B., "An Eight Nucleotide Sequence in the Potato Virus X 3'-UTR is Required for Both Host Protein Binding and Viral Multiplication." 70 *J. Virol*, 5266–5271 (1996)) of the infectious PVX cDNA clone pTXS [Kavanaugh et al., "Molecular Analysis of a Resistance Breaking Strain of Potato Virus X," 189 *Virology*, 609–617 (1992)]. These are shown schematically in FIG. 3A. In these constructs, the expression of the TEV insert is under control of the authentic PVX coat protein subgenomic promoter, and expression of the coat protein is under control of an engineered repeated coat protein subgenomic promoter. The vector PVX5'TEV carries the coding region of the P1/HC-Pro sequence of TEV (nucleotides 146–2674). PVX-HC carries only the region encoding HC-Pro (nucleotides 1057–2433), with a start codon followed by GCC added at the 5' end and a stop codon at the 3'-end of the insert so that the mature HC-Pro protein (with two additional amino-terminal residues) is made without proteolytic processing. PVX-noHC carries the same TEV sequences as PVX-HC except that the translation start site was mutated from AUG to ACG.

These three engineered viruses were used to infect *Nicotiana benthamiana* plants in order to test their ability to cause enhanced pathogenicity. Western analysis indicated that HC-Pro accumulated in leaves infected systemically by either PVX-5'TEV or PVX-HC (FIG. 3B, lanes 2 and 3, respectively), but, as expected, was undetectable in leaves infected with PVX-noHC (FIG. 3B, lane 4). Although PVX-noHC did not express the HC-Pro gene at the protein level, it had not deleted the sequence from the viral genomic RNA as shown by Northern analysis of RNA from systemically infected leaves. A single genomic RNA was detected using hybridization probes specific either for the TEV HC-Pro sequence (FIG. 3C, lane 4) or for the PVX (+) strand genomic RNA (data not shown). Plants infected with PVX-noHC displayed mild symptoms. In contrast, infection of plants with either of the viruses expressing the HC-Pro gene product (PVX-5'TEV or PVX-HC) initially caused vein clearing, followed by necrosis of systemically infected leaves by day 10 post-inoculation, and usually killed the plant. Together, these results indicate that expression of the HC-Pro gene product, but not the RNA sequence itself, is sufficient to induce the increase in PVX pathogenicity. Furthermore, both P1 and P3 coding sequences are dispensable for the detrimental increase in disease symptoms induced by the P1/HC-Pro sequence.

EXAMPLES 11–13

Figure 4:
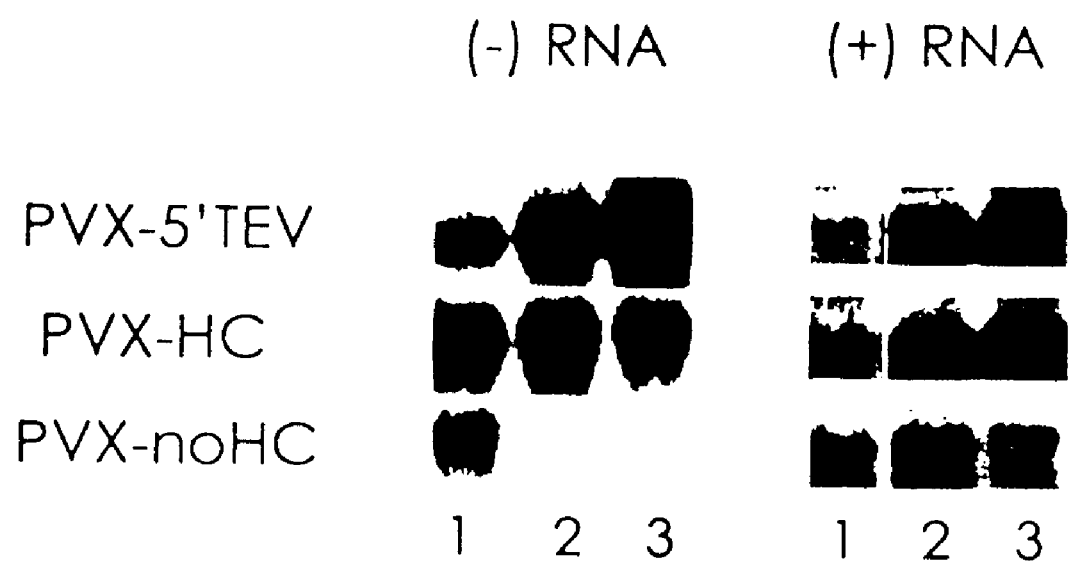
Figure 5:
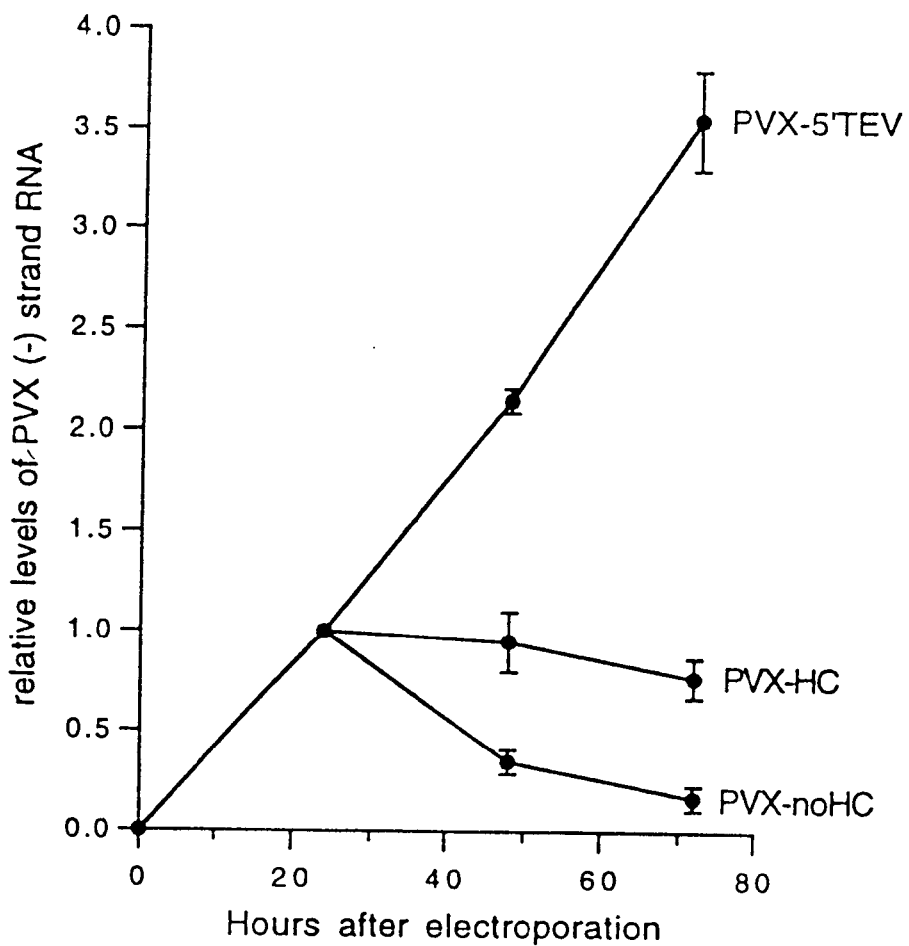

To determine whether the potyviral sequences required for the enhanced pathogenicity of PVX were also required for the boosting characteristics of the sequence, the PVX vectors described above were used to examine the effect of TEV P1/HC-Pro expression on the kinetics of accumulation of PVX (+) and (-) strand RNAs in tobacco protoplasts. Protoplasts were inoculated by electroporation with transcripts of the three engineered PVX cDNAs (FIG. 3A, PVX-5'TEV, PVX-HC and PVX-noHC), and the accumulation of (+) and (-) strand RNA was assayed by Northern analysis at various times after inoculation. The kinetics of (-) strand RNA accumulation in protoplasts infected with PVX-noHC were similar to those previously reported for the parental PVX strain (Sriskanda et al., 1996), with the level of (-) strand RNA peaking at 24 hours after inoculation and then declining to approximately 0.2 times the peak level over the next 48 hours as shown by the Northern blot in FIG. 4 (left side, bottom row) and graphically in FIG. 5. In protoplasts infected with PVX-HC, the level of (-) strand RNA declined only slightly during the same period to a level approximately 0.8 times the 24 hour peak (FIG. 4, left side middle row; FIG. 5). The most striking result, however, was obtained in protoplasts infected with PVX-5'TEV. In this case, the level of PVX (-) strand RNA increased over the entire 72 hour period (FIG. 4, left side, top row), and at 72 hours post-inoculation, the level of (-) strand RNA was 3.6 times higher than the level at 24 hours (FIG. 5). The accumulation of (+) strand RNA in protoplasts infected with PVX-5'TEV and PVX-HC was also prolonged compared to that in PVX-noHC infected cells (FIG. 4, right side, compare top and middle rows to the bottom row). However, as is also true in the mixed infections with TEV and PVX and in the transgenic plant system (Vance et al., 1995), the effect of the TEV sequence on (+) strand RNA accumulation was less dramatic than the effect on (-) strand RNA accumulation. A major effect of TEV P1/HC-Pro expression is to prolong the accumulation of PVX (-) strand RNA.

Thus, unlike the detrimental synergistic enhancement of PVX pathogenicity, which requires only expression of HC-Pro, the boosting effect of the potyviral sequence requires the entire P1/HC-Pro sequence.

EXAMPLES 14–16

Further experiments were conducted to define the regions of P1/HC-Pro required for pathogenicity and booster function. Specific regions of the TEV P1/HC-Pro sequence were mutated and tested for their ability to cause severe disease symptoms when expressed from a PVX vector infecting *N. benthamiana* plants as described above, and for their ability to boost viral replication and accumulation using kinetic analysis of (+) and (-) strand RNAs in tobacco protoplasts. At least one mutation within the region encoding the carboxyterminus of HC-Pro boosted the replication and accumulation of the PVX RNA, but failed to induce the enhanced symptoms in tobacco plants. This mutation was a point mutation which results in a single amino acid change within the active site of the HC-Pro proteinase domain.

These results indicate that the booster sequence may be modified such that its beneficial boosting characteristics are exploited in the absence of the detrimental influence on plant disease symptoms.

The introduction of the claimed booster sequence to the presence of the system containing a foreign gene or endogenous plant gene can be accomplished by several different known methods. For example, the booster sequence can be introduced into the viral vector itself and then the booster sequence-carrying viral vector introduced into the host plant. Alternatively, a transgenic host plant may be used to express the booster sequence. In this method, the transgenic host plant producing the booster sequence is infected with the viral vector. Another method of introduction is known as "co-infection", which involves combining into the host plant a virus that is producing the booster sequence and a virus that is producing the foreign gene or endogenous plant gene of interest. In addition, a two-component co-infection system may be employed. In this process, two defective viruses are co-inoculated into a host plant. One virus will ultimately express the booster sequence and the other will express the foreign or endogenous plant gene of interest. Until these viruses are combined, neither virus viably replicates. However, upon combining, the viruses create the synergistic enhancement of gene expression referred to herein. Finally, a transient expression system may be employed. In this process, a plasmid is introduced into the plant cell. The plasmid replicates and expresses the booster sequence in a transient fashion, but is not stably incorporated into the host plant genome as with transgenic plants described herein. From a broad standpoint, the present invention is not limited to any one type of booster-introduction method.

An exemplary expression method employing a gene product introduced via a viral vector wherein the same viral vector supplies the booster sequence will now be described. Techniques that have been developed to construct viral vectors containing foreign or endogenous plant nucleic acid sequences are well documented. Among such methods include those described in U.S. Pat. No. 5,589,367, which has already been incorporated herein by reference, as well as U.S. Pat. No. 4,855,237, which is also being incorporated herein by reference. Either of the methods described in those patents or various other known methods of constructing viral vectors with foreign genes in them would meet the requirements for use in the presently claimed method when employing viral expression vectors to express the foreign gene products.

EXAMPLES 17–18

The following are examples of employing a viral expression vector with the present booster sequence to achieve enhanced expression of foreign gene products. Two PVX viral vectors were constructed. In these vectors, the luciferase gene was the foreign gene of interest and was cloned into the PVX vector to replace the PVX coat protein gene. Luciferase was expressed from the coat protein subgenomic promoter. The booster sequence from TEV was also expressed from the same PVX vector. In one vector, a functional booster sequence was expressed along with the luciferase (PVX-5'TEVluc). In the other PVX vector, a nonfunctional mutated version of the booster sequence was expressed along with the luciferase [PVX-5'TEV(K)luc]. The K mutation eliminated the boosting capacity of the booster sequence.

To test whether the expression of the foreign gene product would be enhanced or prolonged in the presence of the functional booster sequence, protoplasts were inoculated with transcripts of the two viruses, PVX-5'TEVluc and PVX-5'TEV(K)luc, and luciferase activity was assayed at different times during post-inoculation.

Figure 6:
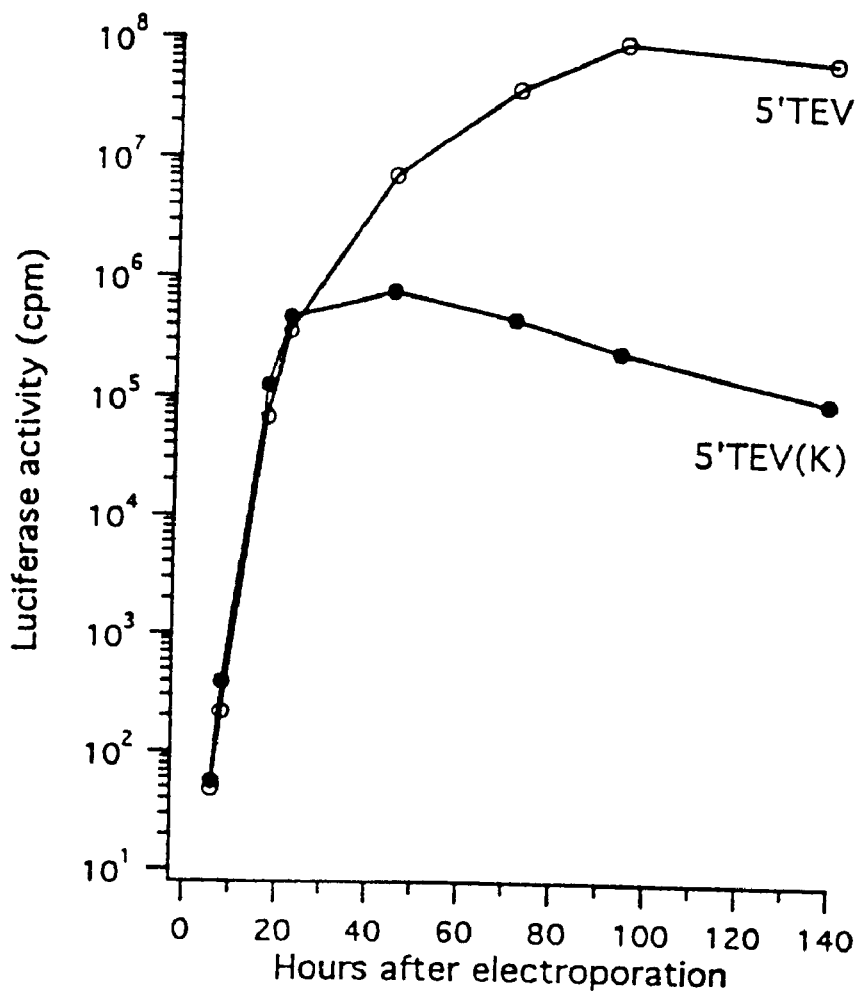

In the protoplasts infected with PVX-5'TEV(K)luc, luciferase activity increased exponentially for approximately 20 hours after inoculation and then began to level off (FIG. 6). In contrast, luciferase activity in protoplasts infected with PVX-5'TEVluc continued to increase until approximately 96 hours after inoculation, reaching a peak level more than 100-fold greater than that in cells infected with PVX-5'TEV(K)luc. These results indicate the ability of the P1/HC-Pro booster sequence to enhance the expression of a foreign gene in plant cells.

The ability of the booster sequence to enhance expression of the foreign gene luciferase was tested in tobacco protoplasts rather than whole plants because the particular PVX vector lacked coat protein and, therefore, could not move within the plant. However, this particular set of circumstances is not to be construed as limiting, but as an example demonstrating the capability of the booster sequence to enhance expression of a foreign gene product in a plant cell when the gene is introduced on a virus vector. Obviously, this would apply to whole plants as well as the tested protoplasts.

More specifically, the present Example involved the use of an infectious cDNA clone of the UK-3 strain of PVX obtained from Dr. David Baulcombe of the Sainsbury Institute in Norwich, UK. This clone served as the base for production of infectious PVX cDNAs viral vectors carrying foreign gene products. The PVX reporter virus PVX-5'TEVluc was constructed using PCR to amplify the luciferase encoding region of pTXS-luc, a PVX vector described in Sriskanda et al., (1996). The amplified fragment comprising the luciferase coding region was digested with Sal I and Xho I and cloned into the Xho I site of a PVX vector carrying the booster sequence under control of the coat protein subgenomic promoter and lacking most of the PVX coat protein coding sequence. The "K" mutation was introduced by replacing an internal Spe I fragment within the HC-Pro coding region of pTXS5'TEVluc with the corresponding fragment from a TEV cDNA containing a nine nucleotide insertion that introduced an Nco I site and resulted in the insertion of the amino acid triplet Thr-Met-Ala immediately after amino acid 426 of the expressed TEV polyprotein.

Capped transcripts of PVX-5'TEVluc and PVX5'TEV(K) luc were synthesized from the two infectious PVX cDNAs described above using the Promega Ribomax T7 transcription kit with the rGTP concentration reduced to 3.75 mM and the addition of 3.75 mM CAP analog distributed by New England Biolabs. Protoplasts were prepared from NT-1 suspension culture cells at the logarithmic stage of growth and electroporated with viral transcripts exactly as previously described in Sriskanda et al. (1996). Luciferase activity from protoplasts infected with either PVX-5'TEVluc or PVX-5'TEV(K)luc was assayed as previously described by Sriskanda et al. (1996), using the Promega luciferase assay kit.

EXAMPLE 19

In this Example, an exemplary expression method wherein the booster sequence is supplied via expression from a stably transformed host plant and a foreign gene is introduced via viral vector is described. Infectious TMV clones carrying the green fluorescent protein (GFP) were derived by cloning the GFP coding sequence into a unique Xho I site of an infectious TMV cDNA termed p30B, a derivative of a previously described infectious cDNA pTB2 (Donson et al., "Systemic Expression of a Bacterial Gene by a Tobacco Mosaic Virus-Based Vector," 88 Proc. Natl. Acad. Sci. USA, 7204–7208 (1991)). The inserted GFP gene is expressed under control of the TMV coat protein promoter and is located just upstream of the Odontoglossum ringspot virus (ORSV) coat protein which substitutes for the TMV coat protein in this infectious cDNA and is expressed from its own subgenomic promoter. The TMV vector was used to introduce the GFP gene into two kinds of tobacco plants, the U-6B transgenic tobacco line and vector only transformed control tobacco plants. U-6B transgenic plants and vector-only control plants were transgenic lines in Nicotiana tabacum cv Havana 425 and have been previously described in Carrington et al. (1990) and Vance et al. (1995). The U-6B plants express the TEV booster sequence from a single DNA copy stably incorporated into the tobacco genome.

The TMV-GFP vector was able to infect the control tobacco plants and express GFP in the inoculated leaf. The viral vector could move systemically to upper noninoculated leaves as evidenced by symptoms of virus infection in the form of mottling on the upper leaves. However, the level of GFP production in the infected upper leaves was very low. In contrast, the TMV-GFP vector infection of U-6B plants resulted in a high level of GFP expression in both inoculated and upper noninoculated leaves. Thus the booster sequence enhanced expression of the foreign gene GFP when introduced via a viral vector. The mode of enhanced expression may be enhanced replication of the viral vector allowing production of more viral RNAs expressing the introduced gene, enhanced stability of the inserted GFP gene in the viral vector, enhanced movement of the viral vector carrying the GFP gene to upper parts of the plant, or some combination of these factors.

EXAMPLE 20

The present Example sets forth an exemplary method for enhancing expression of an endogenous plant gene or a foreign gene (or a portion of a foreign or endogenous gene) that has been introduced to a plant as a fusion to a viral protein expressed from a viral vector. A viral vector expressing a foreign gene or an endogenous plant sequence as a fusion to the coat protein of the virus, such as the vector described in Sugiyama, Hamamoto, Takemoto, Watanabe, Okada, "Systematic Production of Foreign Peptides on the Particle Surface of Tobacco Mosaic Virus," 359 *FEBS Lett.*, 247 250 (1995), is one such example. The viral vector may be used to infect a transgenic plant host that supplies the booster sequence via expression from stably incorporated DNA copies of said booster sequence, for example the U-6B transgenic tobacco plants described herein. The expression of the foreign peptides fused to the viral coat protein would be enhanced.

Other gene product-producing vectors to which the presently described booster sequence could be supplied include those described Hamamoto, Sugiyama, Nakagawa, Hashida, Matsunaga, Takemoto, Watanabe, Okada, "A New Tobacco Mosaic Virus Vector and Its Use for the Systematic Production of Angiotensin-I-Converting Enzyme Inhibitor in Transgenic Tobacco and Tomato." 11 *Bio/Technology* 930 932 (1993); Takamatsu, Watanabe, Yanagi, Meshi, Shiba, Okada, "Production of Enkephalin in Tobacco Protoplasts Using Tobacco Mosaic Virus RNA Vecto," 269 *FEBS Lett.* 73–76 (1990).

EXAMPLES 21–26

It has been determined that the potyviral P1/HC-Pro sequence interferes with the induction of a cellular host system involved in post-transcriptional gene silencing (the cosuppression phenomenon described earlier) of transgenes in higher plant systems. The model for this type of gene silencing states that high level expression of a transgene (or a viral RNA sequence) activates an RNA targeting system which then actively destroys the specific RNA target. The experiments described below exploit a sense RNA-mediated virus resistance system in which plants that post-transcriptionally silence a gene are resistant to a virus carrying that gene to show that the P1/HC-Pro sequence interferes with some aspect of cosuppression.

The particular system used in these experiments employed a tobacco line transformed with a nontranslatable β-glucuronidase (GUS) gene (line 407). Line 407 plants were resistant to a TEV vector carrying the GUS gene and are referred to as being cosuppressed for the GUS gene. However, these plants were susceptible to TEV carrying the green fluorescent protein (GFP) gene. Line 407 plants were crossed individually with three tobacco lines: nontransformed tobacco, line 407 and line TEV B. TEV B plants express the TEV P1/HC-Pro sequence (Verchot and Carrington, (1995)) and are able to mediate synergistic disease when infected with PVX, as described herein (Examples 5–7. FIG. 2).

Offspring of the three individual crosses were inoculated with TEV-GUS and TEV-GFP and examined for expression of the reporter gene which is indicative of viral replication. Offspring of the 407/nontransformed cross and those from the 407/407 cross were susceptible to the control TEV-GFP virus, but resistant to TEV-GUS. In contrast offspring from the 407/TEVB cross were susceptible to both viruses. This result shows that expression of the P1/HC-Pro sequence interferes with the induction or action of the RNA targeting system which invokes sense RNA-mediated resistance and indicates that the described booster sequence can be used to boost the expression of genes introduced to the plant via either stable incorporation into the host genome or via a viral expression vector.

EXAMPLE 27

In order to determine whether the booster sequence will function to enhance expression of a stably incorporated transgene, the present Example may be conducted. A plant is first transformed by any mode of stable transformation with an endogenous plant gene for the purpose of over expressing that particular gene. A portion of the transformants would be cosuppressed for the introduced gene and would fail to express gene product. These cosuppressed plants are then crossed with a plant stably transformed with the booster sequence, such as the U-6B plants described herein. The offspring of the cross would express the previously silenced (cosuppressed) introduced endogenous gene.

EXAMPLE 28

The following Example describes the present method being utilized to express high levels of an endogenous gene product. A plant stably transformed with one or more copies of the booster sequence such as the U-6B plants described herein is subsequently transformed with an additional copy or additional copies of an endogenous gene for the purpose of over-expressing that gene product. The transformants would display high levels of expression of the introduced gene product and/or reduced numbers of cosuppressed offspring that fail to express the gene product.

Gene Product Extraction Methods

As with the introduction of the booster sequence, any number of known extraction methods may be employed to remove the foreign gene product from the host plant for beneficial use in certain applications. The particular protein extraction method will vary depending on the nature of the foreign protein being expressed. If the foreign protein is expressed in the viral vector as a fusion with the viral coat protein, the foreign sequence will be part of the structure of the virus particle and will be isolated by known procedures for isolation of the particle being used as a vector. For example, if α-Trichosanthin is the particular product being isolated, the purification procedure described in Kumagai, et al. (1993) is one that could be used. In some cases, however, the booster sequence-driven expression will result in desirable qualities for the plant host itself. Obviously, in these instances, extraction for the expressed gene product(s) is not desired.

As described above, the potyviral 5'-proximal sequence has been shown to mediate the increased pathogenesis and accumulation of heterologous viruses such as PVX, TMV, and CMV. The present invention uses that sequence in a beneficial manner to enhance the expression of foreign or endogenous gene products from plants and may be used to produce beneficial plant characteristics conferred by the expressed introduced gene product or to produce beneficial gene products for extraction from the plant, such as drugs and the like.

Many of the examples and procedures herein have been discussed in terms of using a viral expression vector to introduce foreign or endogenous plant genes into a tobacco host plant. It is to be understood, however, that the present invention is not so limited, but applies to any method of using the claimed booster sequence to enhance production of an introduced gene product via any plant viral vector or via expression from one or more DNA copies of a gene stably incorporated into the plant genome. Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged both in whole or in part.

What is claimed is:

1. In a method of expressing a foreign gene or an endogenous plant gene that has been introduced into plant cells, plant protoplasts, or whole plants, the improvement comprising the supplying of a booster sequence comprising the coding region for P1, helper component-proteinase (HC-Pro) and a portion of P3, so that said booster sequence includes the region encoding the protein cleavage site required for autoproteolytic processing of the HC-Pro carboxy-terminus of the genome of a potyvirus to said plant cells, plant protoplasts, or whole plants so that expression of said foreign gene or endogenous plant gene is enhanced as compared to said expression in said plant cells, plant protoplasts, or whole plants without said booster sequence.

2. The method of claim 1 wherein said introduced gene is a foreign gene that was not naturally occurring in said plant cells, plant protoplasts, or whole plants prior to being introduced therein.

3. The method of claim 1 wherein said introduced gene is an endogenous plant gene that was naturally occurring in said plant cells, plant protoplasts, or whole plants, prior to being introduced as an additional copy or additional copies of the endogenous gene.

4. The method of claim 1 wherein the booster sequence is expressed independently.

5. The method of claim 1 wherein the booster sequence is fused to other sequences.

6. A method of enhancing expression of a foreign gene or endogenous plant gene that has been introduced into plant cells, plant protoplasts, or whole plants, by supplying a booster sequence to said plant cells, plant protoplasts, or whole plants, such that said expression is enhanced as compared to said plant cells, plant protoplasts, or whole plants without said booster sequence, and then extracting a gene product coded by said foreign gene or endogenous plant gene from said plant cells, plant protoplasts, or whole plants, said booster sequence comprising the 5' proximal region of the genome of a potyvirus, said 5' proximal region comprising the coding region for P1, helper component-proteinase (HC-Pro) and a portion of P3, so that said booster sequence includes the region encoding the protein cleavage site required for autoproteolytic processing of the HC-Pro carboxy-terminus of the genome of a potyvirus, expressed either independently or as a fusion to another sequence.

7. The method of claim 6 wherein said introduced gene is a foreign gene or endogenous plant gene introduced via a viral expression vector and said booster sequence is supplied by expression from the same viral vector.

8. The method of claim 6 wherein said gene is a foreign gene or endogenous plant gene introduced via a viral expression vector and said booster sequence is supplied by expression of one or more DNA copies of said booster sequence stably incorporated into the plant's genome.

9. The method of claim 6 wherein said gene is a foreign gene or endogenous plant gene introduced via a viral expression vector and said booster sequence is expressed from a transient expression system containing one or more DNA copies of said booster sequence.

10. The method of claim 6 wherein a two-component viral vector system is utilized with one viral component expressing said booster sequence and the other viral component expressing said introduced gene.

11. The method of claim 6 wherein said introduced gene is a foreign gene or endogenous plant gene introduced via a viral expression vector and said booster sequence is supplied by co-infection with a potyvirus that expresses the native booster sequence encoded by that potyvirus.

12. The method of claim 6 wherein said gene is a foreign gene or endogenous plant gene introduced via a viral expression vector and said booster sequence is supplied by co-infection with a potyvirus that expresses a nonnative version of said booster sequence.

13. The method of claim 6 wherein said foreign gene or endogenous plant gene is introduced via a viral expression vector having said gene fused to the structural gene of said viral expression vector.

14. The method of claim 6 wherein said foreign gene or endogenous plant gene is introduced to said plant genome via any mode of stable transformation of one or more DNA copies of said introduced gene, and said booster sequence is supplied prior to introduction of said foreign gene or endogenous plant gene via stable transformation procedures and enhances either the expression of the introduced gene product or the number or proportion of transformant plants that express said introduced gene product.

15. The method of claim 6 wherein said foreign gene or endogenous plant gene is introduced to said plant genome via any mode of stable transformation of one or more DNA copies of said introduced gene into the plant genome, and said booster sequence is supplied during the process of introduction of said foreign gene or endogenous plant gene via stable transformation procedures and enhances either the expression of the introduced gene product or the number or proportion of transformant plants that express said introduced gene product.

16. The method of claim 6 wherein said foreign gene or endogenous plant gene is introduced said plant genome via any mode of stable transformation of one or more DNA copies of said introduced gene into the plant genome, and said booster sequence is supplied after introduction of said foreign gene or endogenous plant gene via stable transformation procedures and enhances either the expression of the introduced gene product or the number or proportion of transformant plants that express said introduced gene product.

17. The method of claim 14 wherein said booster sequence is supplied via expression from one or more DNA copies of the booster sequence stably incorporated into the plant genome.

18. The method of claim 15 wherein said booster sequence is supplied via expression from one or more DNA copies of the booster sequence stably incorporated into the plant genome.

19. The method of claim 16 wherein said booster sequence is supplied via expression from one or more DNA copies of the booster sequence stably incorporated into the plant genome.

20. The method of claim 6, wherein said gene product is a drug.

21. A method of enhancing expression of a foreign gene or endogenous plant gene that has been introduced into plant cells, plant protoplasts, or whole plants, by supplying a booster sequence encoding the HC-Pro protein to said plant cells, plant protoplasts, or whole plants so that expression of said foreign gene or endogenous plant gene from said plant cells, plant protoplasts, or whole plants is enhanced as compared to said-expression in said plant cells, plant protoplasts, or whole plants without said booster sequence, said booster sequence comprising the 5' proximal region of the genome of a potyvirus, said 5' proximal region comprising the coding region for P1, helper component-proteinase (HC-Pro) and a portion of P3, so that said booster sequence includes the region encoding the protein cleavage site required for autoproteolytic processing of the HC-Pro carboxyterminus of the genome of a potyvirus, expressed either independently or as a fusion to another sequence.

22. A method as in claim 21, wherein a product of said foreign or endogenous plant gene is extracted.

* * * * *